United States Patent [19]

Buhr

[11] 4,189,323
[45] Feb. 19, 1980

[54] RADIATION-SENSITIVE COPYING COMPOSITION

[75] Inventor: Gerhard Buhr, Königstein, Fed. Rep. of Germany

[73] Assignee: Hoechst Aktiengesellschaft, Fed. Rep. of Germany

[21] Appl. No.: 899,272

[22] Filed: Apr. 24, 1978

[51] Int. Cl.$^2$ ............................................. G03C 1/68
[52] U.S. Cl. ................................... 430/281; 544/216; 544/217; 430/282; 430/285; 204/159.15
[58] Field of Search ............... 96/88, 90 R, 115 P, 96/115 R; 544/216, 217

[56] References Cited

U.S. PATENT DOCUMENTS

| | | | |
|---|---|---|---|
| 3,042,519 | 7/1962 | Wainer | 96/90 R |
| 3,169,963 | 2/1965 | Peters et al. | 544/216 |
| 3,779,778 | 12/1973 | Smith et al. | 96/115 R |
| 3,808,006 | 4/1974 | Smith | 96/90 R |
| 3,987,037 | 10/1976 | Bonham et al. | 544/216 |

FOREIGN PATENT DOCUMENTS

| | | | |
|---|---|---|---|
| 682391 | 9/1939 | Fed. Rep. of Germany | 544/216 |
| 2610842 | 9/1976 | Fed. Rep. of Germany | 96/115 R |

OTHER PUBLICATIONS

Wakabayashi, et al., "Studies On S-Triazines" Bulletin of the Chem. Soc. of Japan, vol. 42, 2924–2930, (Mar. 1969).
Chem. Abs., vol. 83, 1975, 69119b.
Research Disclosure, Sep. 1976, 14957.

*Primary Examiner*—Won H. Louie, Jr.
*Attorney, Agent, or Firm*—James E. Bryan

[57] ABSTRACT

This invention relates to a radiation sensitive composition which comprises, as the radiation sensitive compound, an s-triazine corresponding to Formula I

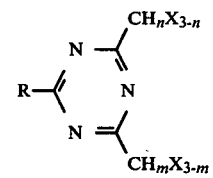

wherein X is bromine or chlorine, and m and n are whole numbers from 0 to 3 which, taken together, do not exceed 5, and in which R is a substituted or unsubstituted bi- or polynuclear aromatic or heterocyclic aromatic group which may be partially hydrogenated and which is linked via an unsaturated nuclear carbon atom.

13 Claims, No Drawings

RADIATION-SENSITIVE COPYING COMPOSITION

The present invention relates to radiation sensitive compositions, in particular copying compositions, which contain light-sensitive organo-halogen compounds whose decomposition under the influence of actinic radiation causes chemical or physical changes in the composition or in one or more of its components.

Radiation sensitive organo halogen compounds are used in industry, on the one hand, for the purpose of utilizing the free radicals formed under the influence of radiation for initiating polymerization reactions or color changes, and, on the other hand, for effecting secondary reactions caused by the liberated acid.

Hitherto known organo halogen compounds belong to a wide variety of chemical compounds.

Despite wide differences in their structure, the hitherto known organo-halogen compounds do not meet the requirements for optimum sensitivity within the main emission range of the light sources presently used in the art, i.e. the known compounds have their UV absorption maxima at relatively low wavelength ranges.

Although some undesirable characteristics are eliminated by the chromophore-substituted vinyl halogen methyl-s-triazines disclosed in German Offenlegungsschriften Nos. 2,243,621 and 2,306,248, they have the disadvantage that their preparation is relatively complicated. Thus, 2-methyl-4,6-bis-trichloromethyl-s-triazine, for example, must be first obtained by co-trimerization of acetonitrile and trichloro acetonitrile, and this compound, which is extremely reactive towards nucleophilic compounds, must then be condensed, under the conditions of a Knoevenagel reaction, with aldehydes, some of which have a complicated structure and thus are expensive to prepare. The resulting vinylene group links the triazine group to a chromophore and forms part of the entire chromophoric system which is responsible for the absorption within the visible and long-wave ultraviolet range of the spectrum which is desired.

It is the object of the present invention to provide easily obtainable organo-halogen compounds which are sensitive to actinic radiation and have a good sensitivity in the ultraviolet and short-wave visible range of the spectrum and thus are suitable for use in radiation sensitive compositions.

The present invention relates to a radiation sensitive composition which contains, as the radiation-sensitive compound, an s-triazine corresponding to Formula I:

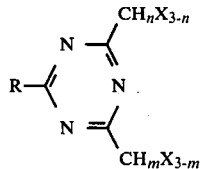

wherein

X is bromine or chlorine, and m and n are whole numbers ranging from 0 to 3 which, taken together, do not exceed 5.

In the composition according to the invention, in this compound, R is a substituted or unsubstituted, bi- or tri-nuclear aromatic or heterocyclic aromatic group which may be partially hydrogenated and which is linked via an unsaturated nuclear carbon atom.

Preferably, the group R is linked via an aromatic carbon atom.

In connection with this application, the term "actinic radiation" means any radiation whose energy at least corresponds to that of short-wave visible light. Long-wave ultraviolet radiation is particularly suitable, but electron and laser beams also may be used.

The symbols in the above Formula I preferably have the following meanings:

R is a bi- or trinuclear condensed aryl group or a corresponding heterocyclic aromatic group with O, S, or N as heteroatoms and may be partially hydrogenated. Alternatively, R may be a diphenyl group. The nuclei of the group R may carry one or more substituents.

X preferably is chlorine, and n and m preferably are zero.

Examples of suitable bi- and trinuclear aromatic groups are:

Naphthalene, anthracene, phenanthrene, quinoline, isoquinoline, benzofuran, benzopyran, dibenzofuran, benzothiophene, dibenzothiophene, acenaphthene, benzoxazole, fluorene, tetrahydrophenanthrene, and dihydrophenalene. Naphthalene is particularly advantageous.

Suitable substituents are, for example:

Halogen, especially chlorine and bromine; lower alkyl groups, preferably with 1 to 3 carbon atoms which may be substituted; substituted or unsubstituted aryl groups; nitro groups; sulfonyl groups; alkyl mercapto groups; phenyl mercapto groups; acyl groups; aryloxy groups; hydroxy groups and, preferably, alkoxy groups. Alkoxy groups with 1 to 8 carbon atoms which, in turn, may be substituted by halogen, phenyl or phenoxy and in which one or more methylene groups may be replaced by O- or S-bridges, and phenoxy, cycloalkoxy, and alkenyloxy groups are particularly advantageous.

Particularly preferred are s-triazines corresponding to Formula I in which R is a group corresponding to Formula II:

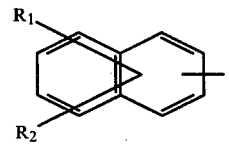

wherein $R_1$ is H or $-OR_3$, but preferably $-OR_3$, $R_2$ is H, Cl, Br, or a lower alkyl, alkenyl, aryl, or a substituted or unsubstituted alkoxy group with 1 to 4 carbon atoms, preferably H, alkyl with 1 to 3 carbon atoms, or alkoxy with 1 to 3 carbon atoms, and $R_3$ is an alkyl group with 1 to 8 carbon atoms which may be substituted by halogen, preferably chlorine or bromine, or by aryl or aryloxy groups, and in which one or more methylene groups may be replaced by O- or S-bridges, or $R_3$ is a cycloalkyl, alkenyl, or aryl group, especially an alkyl or alkoxyalkyl group with 1 to 4 carbon atoms, or $R_1$ and $R_2$ taken together, form an alkylene group which preferably is linked to the naphthalene nucleus in such a manner that a 5- or 6-membered ring results, X is a Cl atom, and n=m=zero.

Compounds in which the s-triazine group and an alkoxy group are arranged in the 1,4 position or the 2,6 position of the naphthalene nucleus of Formula II are of particular advantage.

Because the photochemical activity of the initiators is only insignificantly influenced by the number of carbon atoms in the alkoxy groups, the limitation to 8 carbon atoms in the —$OR_3$ group is not to be regarded as a rigid limit, but may be exceeded, for example by nonyloxy, dodecyloxy, or octadecyl groups.

The following organo halogen compounds are particularly advantageous compounds:

2-(naphth-1-yl)-4,6-bis-trichloromethyl-s-triazine,
2-(4-methoxy-naphth-1-yl)-4,6-bis-trichloromethyl-s-triazine,
2-(4-ethoxy-naphth-1-yl)-4,6-bis-trichloromethyl-s-triazine,
2-(4-butoxy-naphth-1-yl)-4,6-bis-trichloromethyl-s-triazine,
2-[4-(2-methoxyethyl)-naphth-1-yl]-4,6-bis-trichloromethyl-s-triazine,
2-[4-(2-ethoxyethyl)-naphth-1-yl]-4,6-bis-trichloromethyl-s-triazine,
2-[4-(2-butoxyethyl)-naphth-1-yl]-4,6-bis-trichloromethyl-s-triazine,
2-(2-methoxy-naphth-1-yl)-4,6-bis-trichloromethyl-s-triazine,
2-(6-methoxy-5-methyl-naphth-2-yl)-4,6-bis-trichloromethyl-s-triazine,
2-(6-methoxy-naphth-2-yl)-4,6-bis-trichloromethyl-s-triazine,
2-(5-methoxy-naphth-1-yl)-4,6-bis-trichloromethyl-s-triazine,
2-(4,7-dimethoxy-naphth-1-yl)-4,6-bis-trichloromethyl-s-triazine,
2-(6-ethoxy-naphth-2-yl)-4,6-bis-trichloromethyl-s-triazine,
2-(4,5-dimethoxy-naphth-1-yl)-4,6-bis-trichloromethyl-s-triazine,
2-(acenaphth-5-yl)-4,6-bis-trichloromethyl-s-triazine, and, slightly less active,
2-(naphth-2-yl)-4,6-bis-trichloromethyl-s-triazine.

The following are suitable halogen compounds selected from groups which do not come under Formula II:

2-(phenanthr-9-yl)-, 2-(dibenzothiene-2-yl)-, 2-(benzopyran-3-yl)-s-triazine, and the 2-(4-alkoxyanthra-1-yl)-4,6-bis-trichloromethyl-s-triazines. The absorption of the last mentioned class of compounds extends beyond 500 nm.

The aryl-halogen-methyl-triazines according to the present invention are prepared, in the simplest manner, by cotrimerization of the aryl carboxylic acid nitriles with halogen aceto nitriles, in the presence of hydrochloric acid and Friedel-Crafts catalysts, e.g. $AlCl_3$, $AlBr_3$, $TiCl_4$, or borotrifluoride etherate, analogously to the method described in "Bull. Chem. Soc. Jap.", 42, 2924, (1969). Other ways of synthesizing the compounds are by reacting aryl amidines with polychloroaza-alkenes, according to the method published in "Angew. Chem." 78, 982 (1966), or by reacting carboxylic acid chlorides or -anhydrides with n-(iminoacyl)-trichloro acetamidines; 2-aryl-4-methyl-6-trichloromethyl-s-triazines also may be easily prepared by the last-mentioned reaction, as is disclosed in British Pat. No. 912,112. Methods for the subsequent chlorination and bromination of alkyl substituents in s-triazines, to form halogen alkyl-s-triazines, and exchange reactions by which bromine atoms in tribromomethyl groups may be replaced by hydrogen and trihalogen methyl groups in s-triazines may be replaced by amino or alkoxy groups are published in "J. Org. Chem.", 29, 1527 (1964). Some of the nitriles used for co-trimerization are commercially available or may be prepared in a simple manner, for example by dehydration of carboxylic acid amides or oximes or by reaction of aromatic bromine compounds with copper-I-cyanide.

Frequently, it is of advantage to react carboxylic acids or activated aromatic compounds first with chlorosulfonyl isocyanates (CSI) and then with dimethyl formamide, in one operation, thus forming the nitriles, after the intermediate formation of carboxylic acid amide-N-sulfochlorides, as described in "Chem. Ber.", 100, 2719 (1967).

Besides the nitriles, from which the bis-trichloromethyl-s-triazines mentioned in the Examples are derived, the following compounds are also suitable as educts, for example:

4-chloro-1-, 5-chloro-1-, 4-bromo-1-, 5-bromo-1-, 2,6-dimethoxy-1-, 2,7-dimethoxy-1-, 5-nitro-1-, 3,6-dichloro-1-, 1-chloro-2-, 5-chloro-2-, 6-bromo-2-, 4-methyl-1-, 5-methyl-1-, 2-ethyl-1-, 3,4-dimethyl-1-, 3,6-dimethyl-2-, 4-isopropyloxy-1-, 4-bromo-3-methoxy-2-, 4-(2-chloropropyl)-1-, 4-allyloxy-1-, 4-cyclohexyloxy-1-, 4-n-octyloxy-1-, 4-phenoxy-1-, 4-p-tolyloxy-1-, 4-benzyloxy-1-, 4-(2-ethylmercaptoethyl)-1-, and 4-phenyl-1-naphthonitrile, and also 4-acetyl-1-, 4-acetoxy-1-, 4-hydroxy-1-, and 4-methylmercapto-1-naphthonitrile; 2-chloro-, 4'-nitro-, 4'-bromo-, 3-bromo-diphenyl-4-carbonitrile, benzothiophene-2-carbonitrile, -5-carbonitrile, and -7-carbonitrile, dibenzothiophene-4-carbonitrile, benzofuran-2- and -3-carbonitrile, dibenzofuran-1-carbonitrile, -2-carbonitrile, and 3-carbonitrile, anthracene-1-carbonitrile and -2-carbonitrile, 4-methyl-anthracene-1-carbonitrile, 3-chloro-anthracene-1-carbonitrile, phenanthreno-1-carbonitrile and -2-carbonitrile, and 3-chloro-phenanthreno-9-carbonitrile, acridine-2-carbonitrile, fluorene-2-carbonitrile, and -4-carbonitrile, quinoline-4-carbonitrile, isoquinoline-5-carbonitrile, benzoxazole-2-carbonitrile, xanthene-4-carbonitrile, acenaphthene-5-carbonitrile, 2,3-dihydrophenalene-6-carbonitrile, and 1,2,3,4-tetrahydrophenanthreno-9-carbonitrile.

With the exception of the unsubstituted 2-naphth-1-yl- and 2-naphth-2-yl-4,6-bis-trichloromethyl-s-triazines, which also are not known as photoinitiators, the aryl-halogen-methyl-s-triazines according to the present invention have not yet been disclosed in the literature.

The new photoinitiators have a wide range of applications. For example, they may be used as highly effective initiators for photopolymerization reactions triggered by free radicals. Suitable monomers undergoing such polyaddition reactions are, for example:

mono- bis-, tris-, and tetraacrylates and -methacrylates of mono- and poly-functional alcohols or phenols, acrylic and methacrylic acid amides derived from mono- or poly-functional amines, further vinyl esters and vinyl amides. Polymerizable compositions of this type may further contain fillers, binders, polymerization inhibitors, dyestuffs, color couplers, plasticizers, adhesion promoters or oxygen absorbing agents, in varying quantities. If the compositions are applied in the form of layers to supports, which may be chemically pretreated, if desired, for example to steel, chromium, copper or brass foils, or to plastic materials, paper, glass, wood, or ceramics, or to a composite material comprising two or more of these materials, the light-sensitive layer also may be covered by a protective coating which inhibits the access of oxygen.

The photoinitiators according to the invention are effective in quantities as low as 0.05 percent of the solids content of the composition, and an increase of this quantity beyond 10 percent is not advisable, as a rule. Preferably, concentrations between 0.4 and 7 percent by weight are used.

Furthermore, the photoinitators according to the invention may be used in those radiation-sensitive compositions which undergo a change in their properties by the action of acid catalysts formed during photolysis of the initiator. In this connection, the cationic polymerization of systems containing vinyl ethers, N-vinyl compounds, such as N-vinyl-carbazole, or special acid-variable lactones is to be mentioned, without precluding, however, that in some of these systems radical-initiated reactions also may take place. Furthermore, amino plastics, such as urea/formaldehyde resins, melamine/formaldehyde reins, and other N-methylol compounds, and phenol/formaldehyde resins are compositions which are hardened by acids. Although it is normal for epoxy resins to be hardened by Lewis acids or by those acids whose anions are less nucleophilic than chloride or bromide, i.e. the anions of the hydrohalic acids formed during photolysis of the new photoinitators, layers composed of epoxy resins and novolaks harden readily in the presence of the aryl-halogen-methyl-s-triazines according to the invention.

As another advantageous property of the new photoinitiators according to the invention, they are capable of causing color changes in colored systems during photolysis, or of initiating color formation in color couplers, e.g. leuco compounds, or of causing bathochromic color displacement or deepening in mixtures containing cyanine, merocyanine, or styryl color bases. Further, in mixtures such as those disclosed in German Offenlegungsschrift No. 1,572,080, which contain a color base, N-vinyl carbazole, and a halogenated hydrocarbon, the halogen compound tetrabromomethane may be replaced by a small percentage, i.e. about 1/40, of its quantity of aryl-bis-trichloromethyl-s-triazine.

Color changes are very desirable for certain techniques, for example in the manufacture of printing plates, because they render it possible to examine the exposed plate even before it is developed. The acid donors disclosed in German Offenlegungsschriften Nos. 2,331,377, and 2,641,100, advantageously may be replaced by the photoinitiators according to the present invention.

Among the compositions according to the invention, those are particularly advantageous, however, which in addition to the aryl halogen methyl-s-triazines, contain, as an essential component, a compound containing at least one C—O—C bond capable of being split up by an acid.

The following substances are mentioned as examples of compounds which can be split up by acids:

A. Compounds containing at least one ortho-carboxylic acid ester- and/or carboxylic acid amide-acetal grouping; the compounds may have a polymeric character and the groupings may be present as connecting elements in the main chain or as lateral substituents.

B. Polymeric compounds containing recurrent acetal and/or ketal groupings in which both carbon atoms in the α-position of the alcohols required for forming the groupings are aliphatic.

Compounds of type A which may be split up by acids are described in detail as components of radiation sensitive copying compositions in German Offenlegungsschrift No. 2,610,842; copying compositions containing compounds of type B are the object of copending application Ser. No. 899,271, filed Apr. 24, 1978 simultaneously with the present application.

Further compounds capable of being split up by acids are, for example, the particular aryl-alkyl-acetals and -aminals disclosed in German Auslegeschrift No. 2,306,248, which are also decomposed by the photolysis products of the aryl-halogen-methyl-s-triazines according to the invention.

Compositions in which molecules which essentially influence the chemical and/or physical properties of the composition by their presence, are directly or indirectly converted into smaller molecules by the action of actinic radiation, normally show an increased solubility, tackiness or volatility in the exposed areas. These areas may be removed by suitable measures, for example by dissolving them away in a suitable developer liquid. In the case of copying compositions, such systems are referred to as "positive-working systems".

The novolak condensation resins found suitable for many positive-working copying compositions were also found suitable and advantageous as an additive to the copying compositions according to the invention and comprising compounds capable of being decomposed by acids. These resins, in particular the more highly condensed resins containing substituted phenols as formaldehyde condensation partners, promote a strong differentiation between the exposed and the unexposed areas of the layer during development. The type and quantity of the novolak resin added may vary with the purpose for which the composition is intended; novolak proportions between 30 and 90 percent by weight, especially between 55 and 85 percent by weight, based on the solids content of the composition, are preferred. In addition thereof, various other resins may be added, besides the novolaks, vinyl polymers, such as polyvinyl acetates, polyacrylates, polyvinyl ethers, and polyvinyl pyrrolidones, which, in turn, may be modified by co-monomers, being preferred. The most favorable ratio of these resins depends on practical requirements and on their influence on the conditions of development; normally, it does not exceed 20 percent of the novolak component. For special requirements as regards flexibility, adhesion, gloss, etc., minor amounts of other substances, such as polyglycols, cellulose derivatives, e.g. ethyl cellulose, wetting agents, dyestuffs, finely divided pigments, and, if necessary, UV absorbers may be added to the light-sensitive composition.

Preferably, development is effected with the aqueous alkaline developers customary in the art, to which small proportions of organic solvents may be added.

The supports mentioned in connection with the photopolymerizable compositions also may be used for the positive-working copying compositions. In addition, the silicon and silicon dioxide surfaces known from microelectronic processes may be used.

The quantity of photoinitiator contained in the positive-working copying compositions also may vary widely, depending on the substance used and the type of the layer. Favorable results are obtained with proportions ranging from about 0.05 percent to about 10 percent, based on the total solids content, proportions between 0.1 and 5 percent being preferred. In the case of layers of more than 10 μm thickness, it is recommended to use a relatively small quantity of acid donor.

In principle, any electromagnetic radiator emitting waves of a wavelength up to about 600 nm is capable of initiating reactions of the described type in the compositions according to the invention. The preferred wavelength range extends from 300 to 500 nm.

The great number of aryl-halogen-methyl-s-triazines with absorption maxima deep in the visible range of the spectrum and absorption ranges extending beyond 500 nm render it possible to select a photoinitiator which is optimally adapted to the light source employed. In principle, however, a sensitization is also possible. Suitable light sources are, for example:

Tubular lamps, pulsed xenon lamps, metal-halide-doped high pressure mercury vapor lamps, and carbon arc lamps. In addition thereto, the light-sensitive copying compositions according to the invention may be exposed in conventional projectors and enlargement apparatuses, to the light of metallic-filament lamps, or by contact exposure under ordinary incandescent bulbs. Alternatively, coherent laser beams may be used for exposure. Shortwave lasers of adequate energy output, for example argon lasers, crypton-ion lasers, dyestuff lasers, and helium-cadmium lasers emitting between 300 and 600 nm were found suitable for the purposes of the present invention. The laser beam is directed by a given, programmed line and/or screen movement.

As a further possibility, the layers according to the invention may be differentiated by irradiation with electron beams. The copying compositions according to the invention—the same as numerous other organic materials—may be thoroughly decomposed and cross-linked by electron beams, so that a negative image is formed after the unexposed areas have been removed by a solvent or by exposure without an original followed by development. In the case of an electron beam of lower intensity and/or higher operating speed, however, the electron beam causes a differentiation toward a higher solubility, i.e. the irradiated areas of the layer may be removed by a developer. The most favorable conditions may be easily ascertained by preliminary tests.

Preferably, the radiation sensitive compositions according to the present invention are used for the manufacture of printing forms, especially offset, halftone gravure, and screen printing forms, but also in photo resists and in so-called dry resists.

The following Examples illustrate the invention in detail. First, the preparation of a number of new aryl carboxylic acid nitriles is described which serve as starting materials from which the photoinitiators are prepared. Then, the preparation of some halogen-methyl substituted s-triazines is described which were found suitable as acid-forming compounds in the copying compositions according to the invention. They were designated as Compounds Nos. 1 to 20 and will be referred to in the Examples by these numbers.

In the Examples, the relation between parts by weight and parts by volume corresponds to that between grams and milliliters. Percentages and proportions are by weight unless otherwise stated.

Preparation of Aryl Carboxylic Acid Nitriles:

The following aryl carboxylic acid nitriles R—CN, which have not yet been disclosed in the literature of the prior art, were prepared analogously to the instructions given in "Chem. Ber.", 100, 2719 (1967), from the corresponding carboxylic acids R—COOH, or directly from the alkoxy aryl compounds R—H, by reaction first with chlorosulfonyl isocyanate and then with dimethyl formamide.

Table 1

| Nitriles R-CN | | | |
|---|---|---|---|
| Nitrile No. | R | Melting Pt. (°C.) | Starting Substance |
| 1 | 4-(2-ethoxy-ethoxy)-naphth-1-yl | oil; distilled in a bulb tube; air bath 130 to 140° C./5 10⁻⁴ Torr | R-H |
| 2 | 4,7-dimethoxy-naphth-1-yl | 109-110 | R-H |
| 3 | 4,5-dimethoxy-naphth-1-yl | 120.5-121.5 | R-H |
| 4 | 5-methyl-6-methoxy-naphth-2-yl | 74-85* | R-H |
| 5 | 4-methoxy-anthrac-1-yl | 143-145 | R-H |
| 6 | 5-methoxy-naphth-1-yl | 89-91 | R-COOH |

*Crude product; purification at the aryl-s-triazine stage.

The starting substance of Nitrile No. 1, 1-(2-ethoxy-ethoxy)naphthalene, with a melting point of 91°-95° C./0.002 Torr, was obtained by alkylating 1-naphthol with ethyleneglycol monoethyl ether/p-toluene sulfonic acid chloride, according to the method described in "Monatshefte Chem.", 82, 588 (1951).

Preparation of bis-Trichloromethyl-s-Triazines

Gaseous hydrochloric acid is introduced, at a temperature between 0° and 5° C., into a solution of 29.1 grams of 1-ethoxy-naphthalene, 100 grams of trichloroacetonitrile, and 1.65 grams of aluminum tribromide while the solution is agitated. After about 2 hours, the mass in the flask has solidified; introduction of the gas and cooling are discontinued. When the reaction mixture is heated to room temperature, it becomes partly liquid again; it is cooled again to 0° C. and gaseous hydrochloric acid is again introduced for two hours. After the mass has again spontaneously heated and was cooled to 0°-5° C., and after further introduction of gaseous hydrochloric acid for 2 hours, the then solid mass is allowed to stand overnight at room temperature. Thereafter, it is dissolved in methylene chloride and shaken out in a small quantity of water. After the solution has been dried over sodium sulfate and the solvent has been removed under reduced pressure, a crude product is obtained which is freed from unreacted portions of the starting material and from tris-trichloromethyl-s-triazine, which is formed by a side reaction, by distillation in a bulb tube ("kugelrohr") apparatus (air bath: 110°-130° C./0.1 Torr). 24.1 grams of a residue are obtained which consists of almost pure 2-(4-ethoxy-naphth-1-yl)-4,6-bis-trichloromethyl-s-triazine, which, after recrystallization from diethyl ether, has a melting point of 154.5°-156.5° C.

The aryl-bis-trichloromethyl-s-triazines listed in Table 2 are prepared analogously, the crude products being in some cases purified by crystallization, in others by additional filtration over silica gel, using methylene-chloride as the solvent and eluent.

Table 2

Aryl-bis-trichloromethyl-s-triazines corresponding to Formula I wherein n = m = O and X = Cl

| Photo-initiator No. | R | Melting Pt. (°C.) | Longwave Absorption Maximum (nm) λmax | log ξ |
|---|---|---|---|---|
| 1[+] | Naphth-1-yl | 128–129 | 363 | 4.05 |
| 2 | 2-Methoxy-naphth-1-yl | 162–165 | 368 | 3.59 |
| 3 | 4-Methoxy-naphth-1-yl | 181.5–183 | 388 | 4.33 |
| 4 | 5-Methoxy-naphth-1-yl | 154–156 | 399 | 3.87 |
| 5 | 4-ethoxy-naphth-1-yl | 154.5–156.5 | 388 | 4.34 |
| 6 | 4,5-Dimethoxy-naphth-1/yl | 165–167 | 416 | 4.16 |
| 7 | 4,7-dimethoxy-naphth-1-yl | 136–137 | 404 | 4.27 |
| 8 | 4-(2-ethoxy-ethoxy)-naphth-1-yl) | 103–105 | 388 | 4.34 |
| 9[++] | Naphth-2-yl | 210–211.5 | 367 | 3.52 |
| 10 | 1-Methoxy-naphth-2-yl | 132–134.5 | 371 | 3.71 |
| 11 | 3-Methoxy-naphth-2-yl | 173–175 | 322 | 4.29 |
|  |  |  | 385 (sh) | 2.98 |
| 12 | 6-Methoxy-naphth-2-yl | 191.5–192 | 351 | 4.27 |
|  |  |  | 374 | 4.28 |
| 13 | 5-Methyl-6-methoxy-naphth-2-yl | 211–214 | 390 | 4.20 |
| 14 | Quinol-3-yl | 201–204 | 317 | 4.28 |
| 15 | Benzopyran-3-yl | 185–188.5 | 405 | 4.04 |
| 16 | 4-Phenyl-phenyl | 149.5–151.5 | 332 | 4.49 |
| 17 | Dibenzothien-3-yl | 243.5–244.5 | 355 | 4.30 |
| 18 | Phenanthr-9-yl | 181–184.5 | 363 | 4.05 |
| 19 | 4-Methoxy-anthrac-1-yl | 221–225 | 446 | 4.24 |
| 20 | Acenaphth-5-yl | 204–205 | 396 | 4.18 |

[+] The melting point of 216–218° C. given in "Bull. Chem. Soc. Jap." 42, 2924 (1969) could not be confirmed.
[++] Literature: 210–212° C.

EXAMPLE 1

An electrolytically roughened and anodized aluminum plate is whirler coated with a coating solution comprising 6.7 p.b.w. of trimethylolethane-triacrylate,
6.5 p.b.w. of a methylmethacrylate/methacrylic acid copolymer with an acid number of 115,
0.12 p.b.w. of photoinitiator No. 5,
64.0 p.b.w. of ethyleneglycol monoethyl ether,
22.7 p.b.w. of butyl acetate, and
0.3 p.b.w. of 2,4-dinitro-6-chloro-2'-acetamido-5'-methoxy-4'-(β-hyroxyethyl-β'-cyanoethyl)-aminoazobenzene, so that a layer weighing 3 to 4 g/m² results after drying. The plate is then provided with a 4 μm thick protective layer of polyvinyl alcohol (Mowiol 4/88, Hoechst AG), exposed for 30 seconds from a distance of 110 cm to the light of a 5 kW metal halide lamp under a line/screen original, and developed with a 1.5 percent solution of sodium metasilicate.

A negative image of the original is thus obtained. A printing run with an offset printing plate made in this manner was stopped after 200,000 copies of good quality had been printed.

EXAMPLE 2

This example describes the manufacture of a negative-working dry resist. A coating solution of 24.9 p.b.w. of a copolymer of 30 p.b.w. of methacrylic acid, 60 p.b.w. of n-hexylmethacrylate, and 10 p.b.w. of styrene,
16.1 p.b.w. of the reaction product of 1 mole of 2,2,4-trimethylhexamethylene-diisocyanate and 2 moles of hydroxyethylmethacrylate,
0.41 p.b.w. of triethyleneglycol dimethacrylate,
0.58 p.b.w. of Photoinitiator No. 3,
0.11 p.b.w. of the dyestuff used in Example 1, and
57.9 p.b.w. of methyl ethyl ketone is whirler coated on a polyethylene terephthalate film in a manner such that the dry layer weighs 25 g/m². The resulting material is laminated in a commercial laminator, at 120° C., onto a support composed of insulating material provided with a 35 μm thick copper layer. After exposing the material for 60 seconds under an original which contains a continuous tone step wedge, besides line and screen motifs, using a 5 kW metal halide lamp as the light source as in Example 1, and development with 0.8 percent sodium carbonate solution, a negative image of the line and screen motif and steps 1 to 5 of the step wedge remain in the form of a relief, while step 6 of the step wedge is partially corroded.

The resist layer is resistant to etching processes, for example with ferric chloride solutions, and the action of electroplating baths used for the production of circuit boards.

EXAMPLE 3

A mechanically roughened aluminum plate is whirler coated with a solution of 4.3 p.b.w. of a phenol-formaldehyde novolak (melting range 110°–120° C., according to DIN 53181),
10.6 p.b.w. of N-vinyl carbazole,
0.24 p.b.w. of 2-(p-dimethylaminostyryl)-benzthiazole,
0.25 p.b.w. of Photoinitiator No. 7, and
84.6 p.b.w. of methyl ethyl ketone.

After drying a light-sensitive layer of 1–2 μm thickness results. The plate is imagewise exposed for 8 seconds as described in Example 1; during exposure, the color shade in the image areas of the layer changes from yellow to orange red. By moving the plate to and fro in a developer solution composed of 0.6 p.b.w. of NaOH,
0.5 p.b.w. of Na$_2$SiO$_3$.5H$_2$O,
1.0 p.w.b. of n-butanol, and
97.9 p.b.w. of completely desalted water, the unexposed areas of the layer are removed within 75 seconds. When the plate is wiped over with greasy ink, the exposed areas of the layer accept ink, so that the plate may be used for printing on an offset machine.

EXAMPLE 4

Example 3 is repeated, except that in the coating solution the styryl color base is replaced by the same quantity by weight of the cyanine color base 2-[1-cyan-3-(3-ethyl-2-benzthiazolylidene)propen-1-yl]-quinoline and that the Photoinitiator No. 7 is replaced by the same quantity of Photoinitiator No. 13 and that a polyester film is used for coating.

By imagewise exposing the material for 16 seconds as described in Example 1, the color of the image areas changes from an initial light red to deep violet.

By wiping over with the developer used in Example 3, the non-image areas are removed. A negative image of the original is thus produced.

This method may be used for the production of color proofing films.

EXAMPLE 5

A mechanically roughened aluminum plate is whirler coated with a layer of the following composition from a 10 percent methyl ethyl ketone solution:

48.3 p.b.w. of an epoxy resin (obtained from epichlorohydrin and Bisphenol A, epoxy equivalent weight 182–194),
48.3 p.b.w. of a cresol-formaldehyde novolak (melting range 105°–120° C. according to DIN 53181),
2.9 p.b.w. of Photoinitiator No. 8, and
0.5 p.b.w. of Crystal Violet.

By 60 seconds' imagewise exposure as in Example 1 and 40 seconds' development with the developer used in Example 3, a negative image of the original is obtained in which the non-image areas are free from scum.

If the epoxy resin is replaced by the same quantity of the above state novolak, a negative image becomes briefly visible during development, but the resistance of the layer to the developer is so poor that the entire layer is dissolved from the support within 30 seconds.

EXAMPLE 6

This example shows how layers containing the new photoinitiators and compounds which are split up by acids, are imaged by means of electron beams:

About 2 μm thick layers of the following composition
74% by weight of the novolak used in Example 5,
22% by weight of the compound split up by an acid,
3.8% by weight of the photoinitiator, and
0.2% by weight of a dyestuff
are applied to mechanically roughened aluminum and are then irradiated with 11 kV electron beams. The irradiated areas are solubilized under the conditions stated in Table 3.

For development, either the developer used in Example 3 or the following developer solution is used:
5.5 p.b.w. of sodium metasilicate.9H$_2$O,
3.4 p.b.w. of trisodium phosphate.12H$_2$O,
0.4 p.b.w. of anhydrous mono-sodium phosphate, and
90.7 p.b.w. of completely desalted water.

Table 3

| Photo-initiator No. | Compound Split up by an Acid | Irradiated Energy (Joule/cm$^2$) | Developer according to Example | Developing Time (seconds) |
|---|---|---|---|---|
| 3 | polyacetal obtained from benzaldehyde and triethyleneglycol | 1–10 · 10$^{-2}$ | 6 | 45 |
| 5 | polyacetal obtained from propionic aldehyde and triethyleneglycol | 1–15 · 10$^{-2}$ | 3 | 10 |
| 8 | bis-diphenoxy methyl-ether of polyglycol 200 | 1–30 · 10$^{-2}$ | 6 | 30 |

EXAMPLE 7

For the preparation of a re-enlargement plate, a solution was prepared from
4.0 p.b.w. of the novolak stated in Example 5,
1.2 p.b.w. of bis-(5-ethyl-5-butyl-1,3-dioxan-2-yl)-ether of polyglycol 200
0.2 p.b.w. of Photoinitiator No. 12,
0.01 p.b.w. of Crystal Violet, and
94.6 p.b.w. of methyl ethyl ketone
and applied, on a centrifuge, to a brushed aluminum plate.

The plate is exposed for 3 minutes under a positive transparency from a distance of 65 cm, using a projector of type Leitz Prado (f=85 mm, 1:2.5) with a 150 watt lamp as the light source. By immersion in the developer used in Example 6, an enlarged positive copy of the black and white line image on the positive transparency is obtained within 30 seconds. The copy may be reproduced by printing in a small offset press.

Similar results are obtained if the above bis-orthoester is replaced by the same quantity of the polymeric acetal of benzaldehyde and triethylene glycol and Photoinitiator No. 12 is replaced by Photoinitiator No. 20.

EXAMPLE 8

A coating solution composed of
4.0 p.b.w. of the novolak used in Example 5,
1.2 p.b.w. of the reaction product of 2,2,5,5-tetrahydroxymethyl-cyclopentanone and ortho-formic acid trimethyl ester,
0.2 p.b.w. of Photoinitiator No. 1,
0.01 p.b.w. of Crystal Violet, and
94.6 p.b.w. of methyl ethyl ketone
is whirler coated onto an electrolytically roughened and anodized aluminum plate in a manner such that a dry layer weight of 2.0 g/m$^2$ results, and the plate is imagewise exposed for 40 seconds under the conditions stated in Example 1 whereupon a pronounced bluish violet-bluegreen contrast becomes visible.

By wiping over with the developer used in Example 6, the plate is developed to a positive image of the original.

In a test run, 140,000 copies of good quality were obtained from the offset printing plate produced.

Comparable results are obtained by replacing Photoinitiator No. 1 by the same quantity of Initiator No. 6, No. 4, or No. 18, or by a mixture of two or all of these Initiators.

EXAMPLE 9

A positive-working photoresist of high layer thickness is produced as follows:
29.6 p.b.w. of the novolak used in Example 5,
8.9 p.b.w. of the bis-(5-ethyl-5-butyl-1,3-dioxan-2-yl)-ether of 2-ethyl-2-butyl-propane-diol,
0.12 p.b.w. of Photoinitiator No. 5, and
2.1 p.b.w. of modified silicon glycol (a commercially available coating auxiliary)
are dissolved in 59.28 p.b.w. of butan-2-one.

This solution is applied, by means of a wire bar No. 40, to the cleaned copper surface of the composite material used in Example 2. By storing the material for 12 hours at room temperature, the solvent is substantially evaporated. The plate is after-dried for 15 minutes at 70° C. by infrared radiation.

A 70 μm thick resist layer is thus produced which is imagewise exposed for 80 seconds under a line original, using the 5 kW metal halide lamp of Example 1 as the light source, and then may be developed within 40 seconds by spraying with a 0.8 percent sodium hydroxide solution.

EXAMPLE 10

The efficiency of the new photoinitiators as acid donors is investigated by incorporating them in a standard composition:
0.5 gram of the novolak used in Example 5,
0.15 gram of the bis-orthoester used in Example 9,
0.025 gram of photoinitiator, and
0.012 gram of Crystal Violet, dissolved in
12.5 ml of methyl ethyl ketone,
are whirler coated onto plates with electrolytically roughened and anodized surfaces to a layer thickness of 1.5 to 2 μm and then imagewise exposed for 40 seconds under the conditions stated in Example 1.

Layers containing Photoinitiators Nos. 2, 9, 10, 11, 15, 16, 17, and 19 can be developed within 30 seconds by moving them to and fro in the developer used in Example 6, while the layer containing Photoinitiator No. 14 requires 1 minute's development with the developer used in Example 3. In all cases a positive copy of the original is obtained.

EXAMPLE 11

Aluminum plates with an electrolytically roughened and anodized surface are whirler coated with a solution of
4.7 p.b.w. of the novolak used in Example 5,
1.4 p.b.w. of the compound capable of being split up by acid,
0.23 p.b.w. of photoinitiator,
0.02 p.b.w. of Crystal Violet, and
93.05 p.b.w. of butan-2-one
in a manner such that, after drying, a layer of about 1.7 μm thickness results. The layers are imagewise exposed over all spectral lines with an argon laser of 25 W output, the laser beam being focussed by a lens on a spot with a diameter of 5 μm. By varying the recording speed of the laser, the sensitivity of each combination is determined. By treatment with the developer used in Example 6, the exposed areas of the layers are dissolved away within 15 to 90 seconds. The trace of the laser may be brought out even more distinctly by inking the unexposed areas with greasy ink.

The following maximum recording speeds were determined:

| Combination | Recording Speed (m/sec.) |
| --- | --- |
| Propionic aldehyde/triethyleneglycol polyacetal-Photoinitiator No. 12 | 50 |
| Benzaldehyde/1,5-pentanediol polyacetal-Photoinitiator No. 5 | 75 |
| Bisorthoester, according to Example 9-Photoinitiator No. 5 | 25 |

It will be obvious to those skilled in the art that many modifications may be made within the scope of the present invention without departing from the spirit thereof, and the invention includes all such modifications.

What is claimed is:

1. A radiation sensitive composition which comprises an ethylenically unsaturated compound capable of undergoing a polymerization reaction initiated by free radicals or a compound whose solubility is changed by the action of an acid and, as the radiation sensitive compound, from about 0.05 to 10 percent, based on the solids content of the composition, of an s-triazine corresponding to Formula I

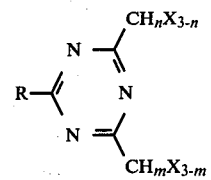

wherein
X is bromine or chlorine, and
m and n are whole numbers from 0 to 3, which, taken together, do not exceed 5,
and in which
R is a substituted or unsubstituted bi- or polynuclear aromatic or heterocyclic aromatic group which may be partially hydrogenated and which is linked via an unsaturated nuclear carbon atom.

2. A radiation sensitive composition according to claim 1 wherein the compound whose solubility is changed by the action of an acid is a compound capable of undergoing a cationic polymerization reaction under the action of acid catalysts.

3. A radiation sensitive composition according to claim 1 in which, in general Formula I R is a group corresponding to Formula II

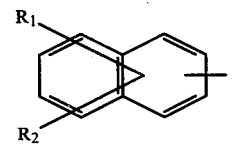

wherein
$R_1$ is H or $OR_3$,
$R_2$ is H, Cl, Br, or an alkyl, alkenyl, aryl, or alkoxy group, and
$R_3$ is an alkyl, cycloalkyl, alkenyl, or aryl group, or
$R_1$ and $R_2$ jointly form an alkylene group,
X is chlorine, and
n and m are zero.

4. A radiation sensitive composition according to claim 1 which contains a compound which comprises at least one C—O—C bond capable of being split up by an acid and whose solubility is increased by the action of an acid.

5. A radiation sensitive composition according to claim 4 which additionally contains a polymeric binder.

6. A radiation sensitive composition according to claim 3 wherein
$R_1$ is $OR_3$,
$R_2$ is H, an alkyl group with 1 to 3 carbon atoms, or an alkoxy group with 1 to 3 carbon atoms, and
$R_3$ is an alkyl or alkoxyalkyl group with 1 to 4 carbon atoms.

7. A radiation sensitive composition according to claim 3, wherein the s-triazinyl group and an alkoxy group are arranged in the 1,4-positions or in the 2,6-positions of the naphthalene nucleus of Formula II.

8. A radiation sensitive composition according to claim 3 wherein the radiation sensitive compound is 2-(naphth-1-yl)-4,6-bis-trichloromethyl-s-triazine.

9. A radiation sensitive composition according to claim 3 wherein the radiation sensitive compound is 2-(4-methoxy-naphth-1-yl)-4,6-bis-trichloromethyl-s-triazine.

10. A radiation sensitive composition according to claim 3 wherein the radiation sensitive compound is 2-(4-ethoxy-naphth-1-yl)-4,6-bis-trichloromethyl-s-triazine.

11. A radiation sensitive composition according to claim 3 wherein the radiation sensitive compound is 2-[4-(2-ethoxy-ethoxy)naphth-1-yl]-4,6-bis-trichloromethyl-s-triazine.

12. A radiation sensitive composition according to claim 3 wherein the radiation sensitive compound is 2-(acenaphth-5-yl)-4,6-bis-trichloromethyl-s-triazine.

13. A radiation sensitive composition according to claim 3 wherein the radiation sensitive compound is 2-(6-methoxy-naphth-2-yl)-4,6-bis-trichloromethyl-s-triazine.

* * * * *

UNITED STATES PATENT OFFICE
CERTIFICATE OF CORRECTION

Patent No. 4,189,323                    Dated February 19, 1980

Inventor(s) Gerhard Buhr

It is certified that error appears in the above-identified patent and that said Letters Patent are hereby corrected as shown below:

Item "[30] Foreign Application Priority Data" has been omitted from the patent, and should read as follows:

- - - April 25, 1977 [DE]   Fed. Rep. of Germany . . . .
          2718259      - - -.

Column 6, line 41, "thereof" should read - - - thereto - - -.

Column 11, line 13, "state" should read - - - stated - - -.

Signed and Sealed this

Seventeenth Day of June 1980

[SEAL]

*Attest:*

SIDNEY A. DIAMOND

*Attesting Officer*    *Commissioner of Patents and Trademarks*